(12) United States Patent
Albertz et al.

(10) Patent No.: US 9,662,619 B2
(45) Date of Patent: May 30, 2017

(54) SYSTEM FOR DISPENSING A FOAM OF A FLUID PRODUCT

(71) Applicant: TWIST BEAUTY PACKAGING AIRSPRAY N.V., Alkmaar (NL)

(72) Inventors: Peter Jozef Jan Albertz, Haarlem (NL); Pierre Dumont, Dargnies (FR); Emmanuel Mauduit, Abbeville (FR); Eric Rossignol, Chalon sur Saone (FR)

(73) Assignee: Twist Beauty Packaging Airspray N.V., Alkmaar (NL)

( * ) Notice: Subject to any disclaimer, the term of this patent is extended or adjusted under 35 U.S.C. 154(b) by 83 days.

(21) Appl. No.: 14/430,110

(22) PCT Filed: Sep. 20, 2013

(86) PCT No.: PCT/EP2013/069648
§ 371 (c)(1),
(2) Date: Mar. 20, 2015

(87) PCT Pub. No.: WO2014/044833
PCT Pub. Date: Mar. 27, 2014

(65) Prior Publication Data
US 2015/0224454 A1    Aug. 13, 2015

(30) Foreign Application Priority Data

Sep. 21, 2012    (FR) ..................... 12 58906

(51) Int. Cl.
*B01F 3/04*        (2006.01)
*B05B 7/00*        (2006.01)
(Continued)

(52) U.S. Cl.
CPC ........ *B01F 3/04446* (2013.01); *B01F 5/0206* (2013.01); *B05B 7/0018* (2013.01);
(Continued)

(58) Field of Classification Search
CPC ... B01F 3/04446; B05B 7/0018; B05B 7/005; B05B 11/04; B05B 11/047
(Continued)

(56) References Cited

U.S. PATENT DOCUMENTS

2002/0153389 A1* 10/2002 Creaghan .............. B05B 7/0037
222/190

FOREIGN PATENT DOCUMENTS

WO    2007086731 A1    8/2007
WO    2009136781 A1    11/2009

OTHER PUBLICATIONS

International Search Report mailed Dec. 2, 2013 (PCT/EP2013/069648); ISA/EP.

* cited by examiner

*Primary Examiner* — Robert A Hopkins
(74) *Attorney, Agent, or Firm* — Banner & Witcoff, Ltd.

(57) ABSTRACT

The invention relates to a system for dispensing a foam of a fluid product (P) comprising a head (3) wherein a mixing chamber (4) of said product with air (A) is formed, said head having: a passage for product (23) and a passage for air (25); a unit for foaming (5); a supply valve (30) of the mixing chamber (4) which comprises a product valve (31) and an air valve (32); a passage for return air (33) which is provided with an air return valve (34); the supply valve comprising a membrane (30) whereon the product (31) and air (32) valves are formed, said membrane being arranged in order to be reversibly mobile starting at a pressure that the source of product (24) or that the source of air (26) exerts on it, between a stable position wherein the passages of the product (23) and of the air (25) are closed by the intermediary of the corresponding valve (31, 32) and a stressed (Continued)

position wherein the passages for product (23) and for air (25) are open in order to supply the mixing chamber (4).

13 Claims, 2 Drawing Sheets

(51) Int. Cl.
  *B05B 11/04* (2006.01)
  *B01F 5/02* (2006.01)
  *B05B 11/00* (2006.01)

(52) U.S. Cl.
  CPC .......... *B05B 7/0025* (2013.01); *B05B 11/043* (2013.01); *B05B 11/047* (2013.01); *B01F 2003/04872* (2013.01); *B01F 2215/0031* (2013.01); *B01F 2215/0032* (2013.01); *B05B 7/0037* (2013.01); *B05B 11/0059* (2013.01)

(58) Field of Classification Search
  USPC ........ 261/28, 34.1, 66, 72.1; 222/181.1, 190
  See application file for complete search history.

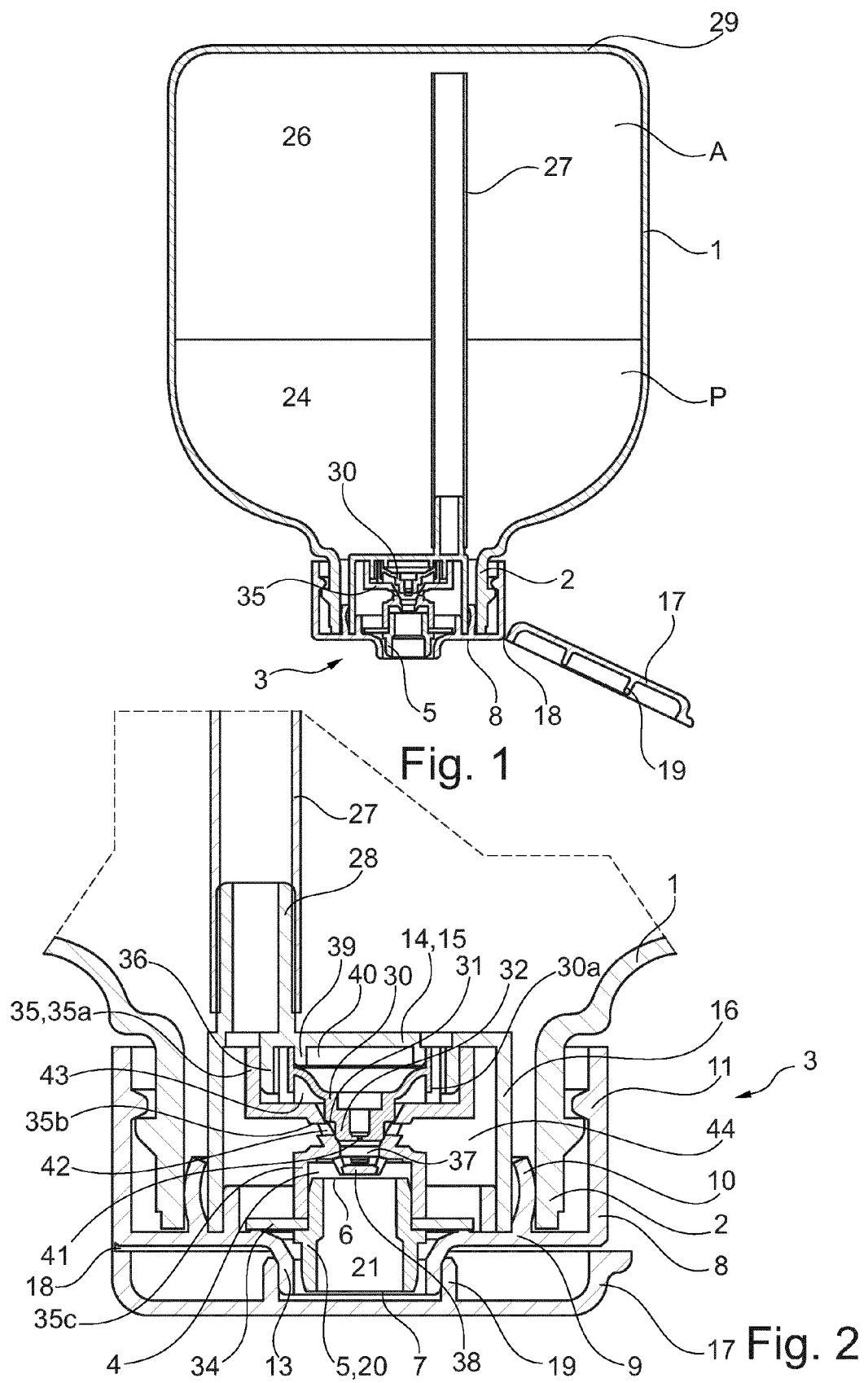

SYSTEM FOR DISPENSING A FOAM OF A FLUID PRODUCT

CROSS-REFERENCE TO RELATED APPLICATIONS

The present application is a U.S. National Phase filing of International Application No. PCT/EP2013/069648, filed on Sep. 20, 2013, designating the United States of America and claiming priority to French Patent Application No. 1258906 filed Sep. 21, 2012. The present application claims priority to and the benefit of all the above-identified applications, which are all incorporated by reference herein in their entireties.

The invention relates to a system for dispensing a foam of a fluid product, in particular liquid, used in perfumery, in cosmetics or for pharmaceutical treatments. The invention further relates to a bottle for dispensing comprising such a system mounted on a reservoir wherein the product and air are conditioned.

In order to allow for the dispensing of the foam, the system comprises a head wherein a mixing chamber of the product with air is formed, as well as a unit for foaming which has a passage for the supply of mixture coming from said chamber and a passage for dispensing the foam.

Supplying the mixing chamber is carried out via the passages respectively for product and for air, said passages being in communication with the reservoir in order to be supplied respectively with product and with air. As such, by providing a deformable reservoir, in particular manually, the conditioned air and product are pressurised in said reservoir in order to supply the mixing chamber by the intermediary of the passages, in order to dispense the product foam without using a pump.

In addition, the deformation of the reservoir is reversible in order to allow for the air return in the reservoir as compensation for the volume dispensed. To do this, a passage for return air is provided between the reservoir and the exterior of the bottle, said passage being provided with an air return valve which is arranged to open under the effect of the vacuum induced by the returning of the reservoir to its initial shape.

In particular in relation with bottles that can be inclined head downwards during storage andor dispensing, it is necessary to provide a supply valve of the mixing chamber in order to prevent product leakage by the head in the absence of stress on the reservoir. Indeed, when the head is arranged underneath the product, i.e. when the bottle is arranged between the horizontal and vertical directions head downwards, simple gravity can suffice to cause a flow of product via the head.

The supply valve conventionally comprises a product valve and an air valve provided respectively on the passage for product and the passage for air, each of said valves being arranged to open the passage for product—respectively for air—in order to supply the mixing chamber starting with a pressure that the product—respectively the air—exerts on it. As such, in the absence of deformation of the reservoir, the supply of the mixing chamber is closed in a sealed manner, with the pressurising of the air and of the product in said reservoir actuating the dispensing of the foam.

However, the use of a supply valve according to prior does not provide full satisfaction, as it is complex to carry out and requires a substantial number of components. In addition, the openingclosing stresses of the different valves are difficult to reconcile, which can result in product leakage andor the dispensing of a foam of which the quality is not always satisfactory, in particular during a slow deformation of the reservoir.

The invention aims to improve prior art by proposing in particular a system that makes it possible, even in relation with a use head inclined downwards, the dispensing of a foam of good quality, wherein the functions of opening/closing the passages of product, of air and of air return are carried out simply and reliably, in particular in relation with a slow deformation of the reservoir.

To this effect, and according to a first aspect, the invention proposes a system for dispensing of a foam of a fluid product comprising a head wherein a mixing chamber of said product with air is formed, said head having:
- a passage for product intended to place in communication a source of product with said chamber and a passage for air intended to place in communication a source of air with said chamber;
- a unit for foaming which has a passage for the supply of mixture coming from the chamber and a passage for dispensing the foam;
- a supply valve of the mixing chamber which comprises a product valve and an air valve provided respectively on the passage for product and the passage for air, each of said valves being arranged to open the passage for product—respectively of air—in order to supply the mixing chamber;
- a passage for return air which is provided with an air return valve arranged to open under the effect of a vacuum that the source of air exerts on it in order to allow for the air return in said source through said head;

the supply valve comprising a membrane whereon the product and air valves are formed, said membrane being arranged to be reversibly mobile starting from a pressure that the source of product or that the source of air exerts on it, between a stable position wherein the passages for product and for air are closed by the intermediary of the corresponding valve and a stressed position wherein the passages for the product and for air are open in order to supply the mixing chamber.

According to a second aspect, the invention proposes a bottle for dispensing a foam of a fluid product comprising a reservoir wherein said product and air are conditioned, said bottle comprising such a system for dispensing which is mounted on said reservoir, said reservoir being reversibly deformable between a pressurised state of the supply valve in order to dispense the foam through the unit for foaming and a vacuum state of the air return valve in order to allow for the air return in said reservoir through the head.

Other objects and advantages of the invention shall appear in the following description, provided in reference to the annexed figures, wherein:

FIG. 1 is a longitudinal cross-section view of a bottle for dispensing according to an embodiment of the invention, said bottle shown in dispensing state;

FIGS. 2 to 4 are enlarged views of the bottle for dispensing of FIG. 1 showing more particularly the system for dispensing in closed state (FIG. 2), in dispensing state (FIG. 3) and in air return state (FIG. 4).

Figure 3:
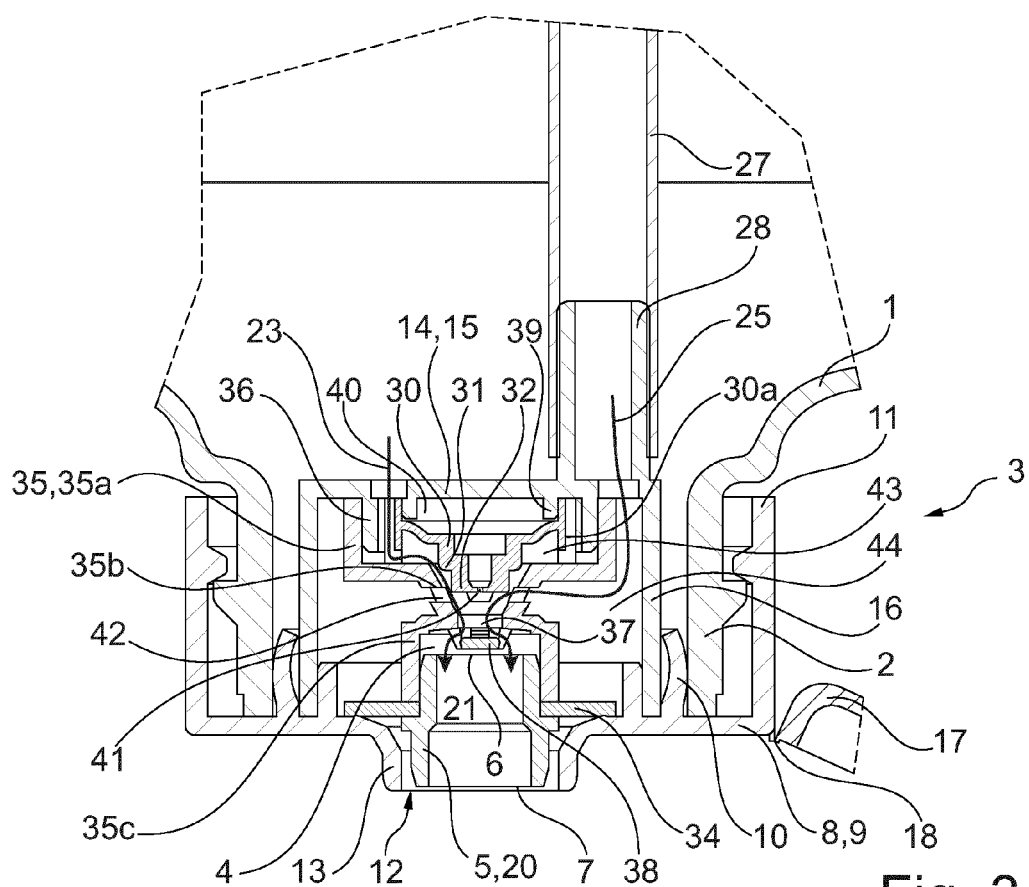

In relation with the figures, a bottle for dispensing a foam of fluid product P, in particular liquid is described hereinbelow, said product able to be of any nature, for example used in perfumery, in cosmetics or for pharmaceutical treatments. The bottle comprises a reservoir 1 surmounted by a neck 2 whereon a system for dispensing is mounted, with the product P and air A being conditioned in said reservoir in order to be mixed for the purposes of dispensing them in the form of foam.

To do this, the system for dispensing comprises a head 3 wherein is formed a mixing chamber 4 of the product P with air A, as well as a unit for foaming 5 which has a passage for supplying 6 with a mixture coming from said chamber and a passage for dispensing 7 the foam to the exterior of the bottle. In particular, the unit for foaming 5 allows for the expansion of the foam and its dispensing at the geometry of the passage for dispensing 7.

In the embodiment shown, the head 3 comprises a support 8 which has an outer plate 9 provided with an inner annular skirt 10 and with an outer annular skirt 11. The skirts 10, 11 are concentric in order to form a space wherein the neck 2 is arranged, with the inner skirt 10 being in sealed contact on the interior of said neck and the outer skirt 11 being snap-fitted onto the exterior of said neck. Other methods of sealed fastening of the head 3 on the neck 2 can be used, for example by screwing or by crimping.

The outer plate 9 comprises a downstream opening 12 formed inside a central wall 13 which extends exteriorly. The head 3 further comprises a base 14 which has an inner plate 15 provided with an outer skirt 16, said skirt associated between the inner skirt 10 and an inside bearing surface which is formed around the downstream opening 12 by extending under the outer plate 9.

Figure 4:
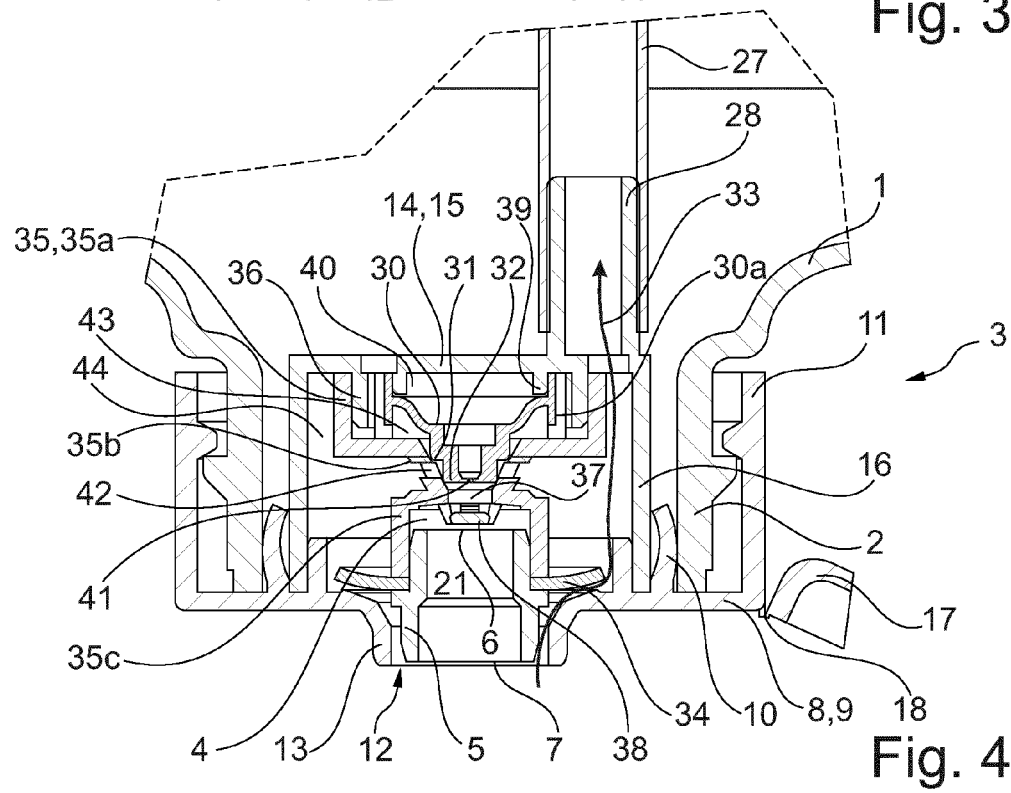

The head 3 comprises a lid 17 for closing the downstream opening 12 between two dispensings, said lid, in the embodiment shown, being mounted by the intermediary of a hinge 18 on an edge of the outer plate 9 between a closed position (FIG. 2) and an open position (FIGS. 1, 3 and 4). In particular, the lid 17 comprises an inner edge 19 which, in closed position, is engaged on the central wall 13 in order to provide the seal of the closing of the downstream opening 12 during storage.

The system for dispensing comprises a casing 20 wherein the unit for foaming 5 is formed. The casing 20 comprises the passages for supplying 6 and for dispensing 7 between which a foaming chamber 21 is formed, in particular in order to allow for the expansion and the dispensing of the foam formed by the mixture of the product P and of air A. Moreover, the passage for dispensing 7 is arranged inside the downstream opening 12 in such a way as to be closed by the lid 17 between two dispensings.

In order create a foam of high quality, the passage for supplying 6 andor for dispensing 7 can be provided with a foaming grid having pores through which the product P—air A mixture passes in order to best expand the foam. The grids can be welded or crimped by creeping of melted material through the mesh, or carried out via injection.

The head has a passage for product 23 in communication with a source of product 24 formed in the reservoir 1 and a passage for air 25 in communication with a source of air 26 formed in said reservoir. In relation with the figures, each passage 23, 25 is formed in the inner plate 15 in the form of an orifice. Alternatively, a passage 23, 25 can include several orifices andor be formed in another wall of the base 14.

The inner plate 15 has an extension 28 surmounting the passage for air 25, with one end of a tubing 27 being mounted on said extension and the other end of said tubing being arranged in the source of air 26 in order to allow for the transport of the air A between said source and said passage for air through the source of product 24. Alternatively, other means for supplying the passage for air 25 can be considered.

In the embodiment shown, the bottle is intended to be used head 3 inclined downwards, with the source of product 24 being formed in the portion of the reservoir 1 located in the extension of the neck 2 and the source of air 26 in that located in the bottom 29 of said reservoir. In particular, this use implies that the head 3 be arranged under the product P, in particular with the bottle arranged between the horizontal and vertical directions head 3 downwards during the dispensing andor storage. In the embodiment shown, the lid 17 has a flat upper wall whereon the bottle is intended to be placed head 3 downwards when stored (FIG. 2).

The system for dispensing comprises a supply valve of the mixing chamber 4 which comprises a product valve 31 and an air valve 32 provided respectively on the passage for product 23 and the passage for air 25. Each of the valves 31, 32 is arranged to open the passage for product 23—respectively for air 25—in order to supply the mixing chamber 4.

The supply valve comprises a membrane 30 which can be made from a flexible sealed material, for example with a base of silicone or elastomer or thermoplastic elastomer (TPE), whereon the product 31 and air 32 valves are formed. The membrane 30 is arranged in order to be reversibly mobile starting from a pressure that the source of product 24 or that the source of air 26 exerts on it, between a stable position wherein the passages for product 23 and for air 25 are closed by the intermediary of the corresponding valve 31, 32 and a stressed position wherein the passages for the product 23 and for air 25 are open in order to supply the mixing chamber 4. In an alternative not shown, the membrane 30 is assisted by an element with a spring effect when it returns to the stable position.

As such, in the absence of sufficient pressure on the membrane 30, in particular via simple gravity, the supply of the mixing chamber 4 is closed in a sealed manner in order to prevent leaks. The pressurising of the membrane 30 actuates the dispensing of the foam by providing that the opening of a valve 31, 32, in particular the product valve 31 under the effect of the pressure of product P on it, causes the joint opening of the other valve 32, 31, and this even if the pressure on said other valve is not enough to cause it to open. Supplying the mixing chamber 4 is then carried out with kinematics and a product/air ratio which are always optimal in order to guarantee the dispensing of a quality foam.

In the embodiment shown, the dispensing of the foam is actuated by the intermediary of the reservoir 1 which is deformable, in particular manually. Indeed, this deformation induces a pressurising of the air A and of the product P which is exerted respectively on the air 32 and product 31 valves in such a way as to supply the mixing chamber 4 then the unit for foaming 5.

In this embodiment, the joint opening of the valves 31, 32 makes it possible to guarantee an optimum supply of the mixing chamber 4 even in the case of slow deformation of the reservoir 1. Alternatively, the source of product 24 andor of air 26 can be pressurised by means other than deforming the reservoir 1, or via a non-manual deformation of said reservoir.

So that the bottle takes back its initial shape between two dispensings, the deformation of the reservoir 1 is reversible, in particular by providing to carry out said reservoir with a shape memory material andor by providing said reservoir with added elastic means. The dispensing of a volume of foam must then be compensated by a return of air of equivalent volume in the reservoir 1.

To do this, the head 3 has a passage for return air 33 which is provided with an air return valve 34 arranged to open under the effect of a vacuum that the source of air 26 exerts on it in order to allow for the air return in said source through said head. In particular, during the air return, the membrane 30 is in a stable position of closing the passages for product 23 and for air 25.

In the embodiment shown, the head 3 comprises an armature 35 that has an internal wall 35a fixed to an exterior bearing surface 36 formed under the inner plate 15 of the base 14. The armature 35 further has a central wall forming a seat 35b for the supply valve wherein the passages for air 25 and for product 23 open, as well as an external wall 35c wherein the mixing chamber 4 is formed.

In the figures, the internal 35a and external 35c walls have a cylindrical geometry of revolution and are connected by the seat 35b which has a tapered geometry, with the diameter of the internal wall 35a being greater than the diameter of the external wall 35c.

Advantageously, the seat 35b has a downstream opening 37 for supplying the mixing chamber 4, said opening being provided with a deflector 38 which is arranged to improve the distribution in the mixing chamber 4 of the air A and of the product P coming from said seat. In particular, the deflector 38 radially directs the flow of air A and of product P in order to distribute it better on the surface of the foaming grid of the passage for supplying 6.

The membrane 30 has an external skirt 30a which is associated with an inside bearing surface 39 formed under the inner plate 15, said membrane having a dome that extends in the armature 35 so that the valves 31, 32 in closed position—respectively open position—are thrust in a sealed manner onto the seat 35b—respectively released from said seat. Alternatively, the skirt 30a can be associated under the inner plate 15 by pinching between two bearing surfaces.

The dome of the membrane 30 has a geometry that is complementary to that of the seat 35b, said dome being displaced axially inn open position in said seat. Moreover, the membrane 30 has an inside chamber 40 which is in communication with the mixing chamber 4 by the intermediary of an orifice 41 passing through said membrane, in particular by being created on the internal end of the dome facing the downstream opening 37 of the seat 35b.

The orifice 41 allows for the escaping of air during the installation of the membrane 30 on the inside bearing surface 39, as well as the compensation of the variations in atmospheric pressure. In addition, the size of the orifice 41 is sufficiently small in order to limit the entry of product P into the inside chamber 40.

The valves 31, 32 are each formed by at least one peripheral lip protruding exteriorly from the dome of the membrane 30, with the lip of the product valve 31 being axially spaced from the lip of the air valve 32. Moreover, the passage for air 25 comprises at least one air duct 42 passing through the seat 35b, the passage for product 23 extends inside said seat. In particular, the air duct 42 is arranged between the lips of the valves 31, 32 in closed position.

In the embodiment shown, a product chamber 43 is formed between the armature 35 and the membrane 30 and an air chamber 44 is formed between the base 14 and said armature, with the passages for air 25 and for product 23 respectively passing through said air and product chambers. To do this, the orifice of the passage for product 23 opens between the inside 39 and outside 36 bearing surfaces, with the orifice of the passage for air 25 opening outside the outside bearing surface 36.

The passage for return air 33 passes through the air chamber 44, with the air return valve 34 able to be displaced in open position of the passage for return air under the effect of a vacuum in the air chamber 44. As such, the air return is carried out through the air chamber 44 in order to supply the reservoir 1 with air A as compensation for the volume dispensed. In particular, the air return is not carried out through the unit for foaming 5 but in parallel of the foaming chamber 21. Moreover, the air pressure in the air chamber 44 during the dispensing induces the closing of the passage for return air 33.

In the figures, the passage for return air 33 extends from the orifice of the passage for air 25 to open between the support 8 and the armature 35, with the air return valve 34 being arranged between said armature and said support. The unit for foaming 5 is fixed in the external wall 35c and the passage for return air 33 opens around the passage for dispensing 7 of said unit for foaming. More precisely, the passage for return air 33 opens annularly between the casing 20 and the central wall 13, the lid 17 closing said passage for return air between two dispensings.

The air return valve 34 is formed of a ring made of elastomeric material, with the inside edge of said ring being pinched between the armature 35 and the casing 20. The outside edge of the ring can be displaced between a thrust closed position of the passage for return air 34 (FIGS. 1 to 3) in order to allow for the storage and the dispensing, and a separated open position of said passage (FIG. 4) in order to allow for the air return. In an alternative not shown, the air return valve 34 can include a ball mounted in a sealed manner on a seat by the intermediary of a retaining cage.

The invention claimed is:
1. System for dispensing a foam of a fluid product comprising a head wherein a mixing chamber of said product with air is formed, said head having:
  a passage for product intended to place in communication a source of product with said chamber and a passage for air intended to place in communication a source of air with said chamber;
  a unit for foaming which has a passage for supplying with a mixture coming from the chamber and a passage for dispensing the foam;
  a supply valve of the mixing chamber which comprises a product valve and an air valve provided respectively on the passage for product and the passage for air, each of said valves being arranged to open the passage for product and for air respectively in order to supply the mixing chamber;
  a passage for return air which is provided with an air return valve arranged to open under the effect of a vacuum that the source of air exerts on it in order to allow for the air return in said source through said head;
  wherein the supply valve comprises a membrane whereon the product and air valves are formed, said membrane being arranged in order to be reversibly mobile starting from a pressure that the source of product or that the source of air exerts on it, between a stable position wherein the passages of product and of air are closed by the intermediary of the corresponding valve and a stressed position wherein the passages for the product and for the air are open in order to supply the mixing chamber;
  wherein the supply valve comprises a seat wherein the passages for air and for product open, the valves in closed position being thrust in a sealed manner onto said seat, and the valves in open position being released from said seat; and
  wherein the membrane and the seat have a complementary tapered geometry, with the membrane being displaced axially in open position.

2. System for dispensing according to claim 1, characterised in that the passage for air comprises at least one air duct passing through the seat, with the passage for product extending inside said seat.

3. System for dispensing according to claim 1, characterised in that the head comprises a base wherein an armature is fixed, said armature having a wall forming the seat and the membrane being associated with the base by being arranged in said armature.

4. System for dispensing according to claim 3, characterised in that the passage for product passes through a product chamber formed between the armature and the membrane, with the passage for air passing through an air chamber formed between the base and said armature.

5. System for dispensing according to claim 4, characterised in that the passage for return air passes through the air chamber, with the air return valve able to be displaced in open position of said passage for return air under the effect of a vacuum in the air chamber.

6. System for dispensing according to claim 5, characterised in that the head comprises a support to which the base is fixed by causing the passage for return air to open between said support and the armature, with the air return valve being arranged between said armature and said support.

7. System for dispensing according to claim 3, characterised in that the mixing chamber is formed inside the armature, with the unit for foaming being fixed to said armature.

8. System for dispensing according to claim 6, characterised in that the passage for return air opens around the passage for dispensing of the unit for foaming.

9. System for dispensing according to claim 1, characterised in that the membrane has an inside chamber which is in communication with the mixing chamber by the intermediary of an orifice passing through said membrane.

10. System for dispensing according to claim 1, characterised in that the valves are each formed by at least one peripheral lip protruding exteriorly from the membrane, with the lip of the product valve being axially spaced from the lip of the air valve.

11. System for dispensing according to claim 1, characterised in that the seat has a downstream opening for supplying the mixing chamber, said opening being provided with a deflector which is arranged to improve the distribution in the mixing chamber of the air and of the product coming from said seat.

12. System for dispensing according to claim 1, characterised in that the passage for supplying and/or for dispensing are provided with a foaming grid.

13. Bottle for dispensing a foam of a fluid product comprising a reservoir wherein said product and air are conditioned, said bottle comprising a system for dispensing according to claim 1 which is mounted on said reservoir, said reservoir being reversibly deformable between a pressurised state of the supply valve for dispensing the foam through the unit for foaming and a vacuum state of the air return valve in order to allow for the air return in said reservoir through the head.

* * * * *